(12) United States Patent
Butler et al.

(10) Patent No.: US 7,553,817 B2
(45) Date of Patent: *Jun. 30, 2009

(54) METHODS FOR IMPROVING CARDIAC FUNCTION

(75) Inventors: Terri L. Butler, Kirkland, WA (US); John St. Cyr, Coon Rapids, MN (US); Clarence A. Johnson, Wyoming, MN (US)

(73) Assignee: Bioenergy, Inc., Ham Lake, MN (US)

( * ) Notice: Subject to any disclaimer, the term of this patent is extended or adjusted under 35 U.S.C. 154(b) by 429 days.

This patent is subject to a terminal disclaimer.

(21) Appl. No.: 10/692,338

(22) Filed: Oct. 23, 2003

(65) Prior Publication Data

US 2004/0087515 A1 May 6, 2004

Related U.S. Application Data

(63) Continuation of application No. 09/917,292, filed on Jul. 27, 2001, now abandoned.

(60) Provisional application No. 60/221,526, filed on Jul. 28, 2000, provisional application No. 60/302,200, filed on Jun. 29, 2001.

(51) Int. Cl.
  *A61K 31/70* (2006.01)
(52) U.S. Cl. ..................................................... 514/23
(58) Field of Classification Search ................... 514/23, 514/25
  See application file for complete search history.

(56) References Cited

U.S. PATENT DOCUMENTS

| | | | | |
|---|---|---|---|---|
| 4,719,201 A * | 1/1988 | Foker | ............................ | 514/23 |
| 4,920,098 A * | 4/1990 | Cotter et al. | .................... | 514/2 |
| 6,054,128 A * | 4/2000 | Wakat | ......................... | 424/765 |
| 6,159,942 A * | 12/2000 | St. Cyr et al. | ................. | 514/23 |
| 6,172,114 B1 * | 1/2001 | McCabe | ...................... | 514/565 |
| 6,218,366 B1 * | 4/2001 | St. Cyr et al. | ................. | 514/23 |
| 6,339,716 B1 * | 1/2002 | Sawada et al. | ............... | 600/407 |
| 6,420,342 B1 * | 7/2002 | Hageman et al. | .............. | 514/23 |
| 6,429,198 B1 * | 8/2002 | St. Cyr et al. | .................. | 514/23 |

FOREIGN PATENT DOCUMENTS

JP 02 286620 A 11/1990

OTHER PUBLICATIONS

Omran et al., "Ribose Improves Myocardial . . . ", Journal of Molecular and Cellular Cardiology, vol. 33, issue 6, p. A173, Jun. 2001.*
Bianco et al., "How congestive heart failure works", howstuffworks.com.*
Omran et al., "Ribose Improves Myocardial . . . ", Journal of Molecular and Cellular Cardiology, vol. 33, issue 6, p. A173, Jun. 2001.*
Cohn, Jay N., MD, Preventing Congestive Heart Failure, American Family Physician, Apr. 15, 1998, vol. 57, Issue 8.*
Pliml, W., Effects of Ribose on Exercise-Indusced Ischaemia in Stable Coronary Artery Disease, The Lancet, Aug. 29, 1992: 340(8818), pp. 507-510.*
Omran et al., Ribose Improves Myocardial Function and Quality of Life in Congestive Heart Failure Patients, Journal of Molecular and Cellular Cardiology, Jun. 2001, vol. 33, No. 6, pp. A173.*
Mahoney, J.R. et al.: "A comparison of Different Compounds . . . " J. of Surg. Res., vol. 47, 1989, pp. 530-534, Acad. Press, San Diego, CA US.
H.-G. Zimmer et al. "Ribose accelerates . . . " J. of Mol. & Cel. Cardiol. vol. 16, 1984, pp. 863-866, Acad. Press, :London, UK.
Loscalzo et al. "Nitric oxide . . . " Progress in Cardiovas. Dis., vol. 38, pp. 87-104, 1995, Saunders, Philadelphia, PA US.
Cyr [sic] et al "Enahnced high energy . . . " J. of Surg. Res., vol. 46 pp. 157-162, 1989 Acad. Press, San Diego, CA, US.
Pliml, W. et al. "Effects of Ribose . . . " The Lancet, vol. 340, pp. 507-510, Lancet Limited, London, UK, 1992.

* cited by examiner

*Primary Examiner*—Traviss C McIntosh, III
(74) *Attorney, Agent, or Firm*—Kathleen R. Terry

(57) ABSTRACT

The present invention relates to compositions for supplementing the diet of subjects suffering from cardiovascular or peripheral vascular disease or those at risk for such conditions. Ribose is given alone or in combination with one or a combination of vasodilators, nutrients and vitamins. Preferred vitamins include Vitamins C, B6, B12 and folic acid. Preferred nutrients include glutamine and glucose.

3 Claims, No Drawings

METHODS FOR IMPROVING CARDIAC FUNCTION

RELATED APPLICATIONS

This application is a continuation of U.S. patent application Ser. No. 09/917,292, filed Jul. 27, 2001, now abandoned which claims priority of U.S. Provisional Patent Application Ser. No. 60/221,526, filed Jul. 28, 2000 and U.S. Provisional Patent Application Ser. No. 60/302,200, filed Jun. 29, 2001.

BACKGROUND OF THE INVENTION

Nutritional therapies are commonly applied in ill people in order to enhance physical capacity and recovery from stresses due to medical conditions. Many times the recommendations simply include dietary advice regarding the distribution of carbohydrates, proteins, and fats in the overall diet. A more advanced approach is to recommend supplementation of key nutrients that will aid healing and enhance the physical state of the individual. Such nutritional formulations may be termed "dietary supplements," "functional foods" or "medical foods." In order to formulate an effective dietary supplement or functional or medical food, an understanding of the scientific basis behind the key ingredients is essential. Once a well-grounded recommendation toward dietary modification is made it can have a powerful influence on the rate of recovery in the individual who is in poor health.

Often, persons who consider themselves to be in good health with a good nutritional status are actually somewhat suboptimal in both parameters, rendering them at risk for developing such medical conditions. Dietary supplements, functional or medical foods developed for improving cardiovascular function may also benefit such persons as cardioprotectors.

In the area of medically recommended supplementation artificial diets have played a key role for many years. Post-surgery, the gastro-intestinal tract of a patient is typically unable to properly digest food for several days. In such cases parenteral nutrition is essential, wherein the patient is given glucose or a carefully formulated mixture of salts, carbohydrates, amino acids, fatty acids, and vitamins. Even after the patient is weaned from parenteral nutrition, enteral nutrition with a similar composition may be established orally or via a feeding tube, or a medical food enteral supplement may be added to his or her diet in order to optimize the types and amounts of nutrients the patient requires and receives.

The most pressing need for improved prevention, rehabilitation and maintenance regimens is in the area of cardiovascular disease, which is the leading cause of death worldwide. It has been projected that one of five persons in the United States has cardiovascular disease. Within this arena, myocardial infarction accounts for more than half a million deaths per year. Furthermore, survivors face a level of morbidity and subsequent disability that affects their medical, social, and of equal importance, economic status. Therefore, surviving the initial acute event of a myocardial infarction leaves patients with a variety of challenges. Such patients may be left in a state of compromised cardiovascular function such as chronic ischemic disease, congestive heart failure or reduced peripheral blood flow.

Congestive heart failure may have a more insidious onset than that following myocardial infarction. Atherosclerosis may gradually lessen circulation to the heart or uncontrolled hypertension may weaken the heart muscle. Another condition, cardiomyopathy, may occur from a variety of causes including ischemia, hypertension or chronic infection. Whatever the cause, these types of cardiovascular disease may present a similar clinical picture and pose the same problems of treatment and maintenance as does myocardial infarction.

Peripheral vascular disease is closely related to cardiovascular disease, in that the same underlying cause, atherosclerosis, may impair circulation to the skeletal muscles, brain or kidneys, interfering with their function. A nutritional supplement that benefits subjects with cardiovascular disease will also benefit these subjects.

Over the past twenty years, cardiac rehabilitation has provided survivors with an increased quality of life. Cardiac rehabilitation programs have continued to change to meet the needs and expectations of these afflicted individuals. An important aspect of successful rehabilitation is a gradual programmed increase in exercise training with an attention to modifying existing cardiac risk factors. The ultimate goal in any cardiac rehabilitation program is the improvement of functional capacity, the lessening of awareness of activity-produced symptoms, the reduction of disability and the modification of known coronary risk factors for the prevention of subsequent cardiovascular events, that is, to provide cardioprotection. Many patients feel strongly that a good quality of life includes the ability to resume their pre-disease activity, if at all possible.

While general nutritional supplementation is the standard mode of therapy as part of a disease management program, a more focused nutritional program can have more specific and powerful benefits. For example glutamine is useful in the treatment of diseases of the liver due to its ability to increase blood flow to the liver (U.S. Pat. No. 6,001,878). Glutamine is also effective at maintaining the immune system. This was shown in a study where there was a lower level of infection in patients following bone marrow transplantation when their parenteral nutritional program was supplemented with glutamine (Calder and Yapoob 1999). Another example is taurine which has a positive inotropic effect on the heart and can be used as a treatment in congestive heart failure. In a clinical trial 4 weeks of taurine supplementation led to a highly significant improvement in dyspnea, palpitation, crackles, edema, and New York Heart Association functional class (Azuma et al 1983).

Several of the vitamins are known to be beneficial in repairing tissue damage and enhancing rehabilitation. Individual patients vary in diet and physiologic needs and thus in the requirement of supplementation. Ideally, each patient could be evaluated for those supplements that are most suboptimal in the diet or for which there is a higher than expected requirement. However, it is impractical to fine-tune supplementation to each patient, and therefore a useful supplement will contain sufficient vitamins to provide adequate daily intake for the majority of prospective patients.

The best therapy for cardiovascular disease is prevention. Hypertension is a prevalent cause of cardiovascular disease. Persistent hypertension is accompanied by left-ventricular hypertrophy and myocardial stiffness. These factors result in left ventricular diastolic dysfunction. Many drugs are marketed to reduce blood pressure, and the current philosophy suggests that combination therapy is preferred to single drug therapy. A nutritional supplement that caused a reduction in blood pressure is desirable.

Thus the need remains to select the best choice of nutrients and the balance of such nutrients as will benefit the majority of subjects both for recovery from cardiovascular disease and for cardioprotection for the prevention of onset or recurrence of cardiovascular disease.

SUMMARY OF THE INVENTION

The present invention relates to compositions and methods for supplementing the diet of subjects who are either recovering from or living with disease or medical injury, or subjects at risk for such disease who are in need of cardioprotection. Examples of such subjects include those with atherosclerosis resulting in cardiovascular disease or peripheral vascular disease, those who suffer from hypertension, myocardial infarction, those who are recovering from surgery, chemotherapy, or other medical trauma or those who are at risk for these conditions.

According to the methods of this invention, D-Ribose (which may be subsequently referred to as "ribose") is administered to a patient at least once a day in unit dosages of from two to ten grams. A preferred method is the administration of a unit dosage of two to eight grams of ribose two or three times a day. The most preferred method is the administration of a unit dosage of five grams of ribose given three times per day. The unit dosage may be dissolved in a suitable amount of water or may be ingested as a powder.

Compositions comprising a vasodilator and ribose are provided. Ribose in a unit dosage of one to 20 grams is administered with an effective amount of a vasodilator. A more preferred dosage of ribose is two to ten grams. A most preferred dosage of ribose is five grams. The vasodilator may be L-arginine, nitroglycerine, nitrates, nitrites, papaverine, isoproterenol, nylidrin, isoxsuprine, nitroprusside, adenosine, xanthine, ethyl alcohol, dipyramide, hydrazaline, minoxidil, diazoxide or analogs of the foregoing. A most preferred vasodilator is L-arginine. The components may be mixed together in a powder for simultaneous administration. When the vasodilator is nitroglycerine, a nitrate or a nitrite, ribose is preferably administered orally about fifteen minutes before the vasodilator is given buccally, sublingually or transdermally. This composition is administered from one to four times daily.

Compositions comprising ribose and vitamins are provided. Ribose in a unit dosage of one to 20 grams is administered along with one or more of vitamins C, B6, B12 and/or folic acid. It is most convenient to prepare ribose and vitamins as a triturated powder. A more preferred unit dosage of ribose to be administered with vitamins is two to 10 grams of ribose. A most preferred unit dosage of ribose to be administered with vitamins is five grams of ribose.

Compositions comprising ribose, a vasodilator and vitamins are provided. Ribose in a unit dosage of one to 20 grams is administered along with a vasodilator and one or more of vitamins C, B6, B12 and/or folic acid. It is most convenient to prepare ribose, a vasodilator and vitamins as a triturated powder. A more preferred unit dosage of ribose to be administered with a vasodilator and vitamins is two to 10 grams of ribose. A most preferred unit dosage of ribose to be administered with vitamins is five grams of ribose. A most preferred composition comprises ribose, L-arginine, and/or folic acid.

Glutamine may be added to each of the above compositions. Dextrose may be added to each of the above compositions in the same amount as ribose, if it is desired to eliminate potential hypoglycemia. L-Carnitine may be added to each of the above compositions. Taurine may be added to each of the above compositions. Creatine may be added to each of the above compositions. Pyruvate may be added to each of the above compositions. Coenzyme Q10 may beaded to each of the above compositions.

A most preferred composition is provided comprising ribose, L-arginine, glutamine, folic acid, glucose, vitamins B12, B6 and C. Ornithine, citrulline or other orally administered vasodilators may be added in place of or in addition to L-arginine. Any one or a combination of L-carnitine, taurine, creatine, pyruvate may be added to the above compositions Any of the compositions of this invention are preferably dissolved in about eight ounces of water and ingested as a solution. Flavorings and other additives may be added to make the solution more palatable. In each of the compositions of this invention, D-ribose in a unit dosage of one to 20 grams is administered two to four times per day. The other ingredients may vary in accordance with recommended daily allowance.

DETAILED DESCRIPTION OF THE INVENTION

The invention comprises compositions that include D-ribose, alone and in combination with a vasodilator. Nutrients that improve cardiovascular function, healing, or have other healthful characteristics are also provided. Those nutrients selected will have effects on metabolic pathways or physiological functions different from those of ribose and thus will have incremental benefit over the basic benefit of ribose alone. Improvement of cardiovascular function results inherently in improvement of a subject's physical capability and hence enhances the subject's quality of life. Therefore, in the present invention, when the term "cardiovascular function" is used, it is understood to include improvement of physical capability and enhancement of quality of life. Nutrients to be used in this invention in combination with D-ribose include, but are not limited to those that may enhance endothelium-dependent vasodilation by acting on nitric oxide release including ascorbic acid, L-arginine, ornithine, citrulline, glutamine, folic acid, vitamin B6 and vitamin B12. Also included are other energy enhancing compounds such as L-carnitine, pyruvate, taurine, and coenzyme Q10.

D-ribose (otherwise referred to as ribose) is a natural 5-carbon sugar found in every cell of the body. It forms part of the backbone of the genetic materials ribonucleic acid and deoxyribonucleic acid as well as part of the basic structure of the body's main energy carrying molecule, adenosine triphosphate (ATP).

During disease or stress, the body's energy resources become depleted. In particular, intracellular levels of ATP can be lowered significantly. Since cells and organs need adequate energy in order to maintain integrity and function, it is essential that the supply of ATP be replenished soon after it is consumed. This is possible over the short term in the presence of oxygen via the respiratory metabolic pathways. However, when the oxygen supply is inadequate because of decreased circulation, even temporarily, energy metabolism is impaired and ATP molecules are not regenerated quickly enough to meet the body's energy demands.

For example, when the myocardium becomes oxygen depleted due to ischemia (restricted blood flow to the heart) resulting from stenotic and/or occluded arteries, heart attack, heart surgery, heart transplantation or other surgery requiring general anesthesia, myocardial levels of ATP will fall dramatically and can take up to 10 days to recover (Ward et al 1984). Under conditions of such energetic depletion myocardial function is compromised and there is an increased risk of permanent loss of myocardial tissue.

Because of its ability to enhance ATP recovery and synthesis ribose can increase exercise capacity in both ill and healthy people. One study found that orally administered high doses of ribose increased the treadmill performance of angina patients (Pliml et al 1992). Another study found that in athletes on exercise bikes, power output was greater in the group that was taking supplemental ribose (U.S. Pat. No. 6,159,942).

Ribose is the key ingredient in the compositions described in this invention. Other energy enhancers might be included that increase the effect of ribose. Nutrients that act by other mechanisms can be energy enhancers that would optimize the nutritional composition. For example, increasing a vessel's diameter would enable blood to reach outlying muscle tissue and thus transport ribose and nutrients to that tissue. Enhancement of other physiological functions in addition to energy would compound the effect of the nutritional composition.

Nitric oxide (NO) is one of the primary inducers of vasodilation and is generated in many of the tissues of the body. It can diffuse across membranes rapidly, thus acting on elements that are some distance from the site of production. NO is synthesized from L-arginine (also referred to as arginine) by the action of NO synthase (NOS), leading to the production of L-citrulline. L-citrulline is then recycled to L-arginine by argininosuccinate synthase and argininosuccinase. Ornithine can serve as a precursor to L-arginine. Many physiological processes are regulated by NO including endothelial vasodilator tone which is essential for the regulation of blood pressure, formation or memory by acting as a neurotransmitter, regulation of various gastrointestinal, respiratory, and genitourinary tract functions by mediating some forms of neurogenic vasodilation, and contribution to and the regulation of cardiac contractility.

In addition, the number of physiological processes in which NO has been implicated is growing rapidly. Beyond what is mentioned above, NO may also be involved in the regulation of muscle function by modulating glucose uptake, mitochondrial oxygen metabolism, blood supply to muscle and contractility. In most cases, muscle NO can be viewed as a positive regulator of muscle function, in that it has been experimentally shown to promote glucose transport and presumably to increase blood supply to muscle through its vasodilatory capabilities. Tidball et al. (1998) found that mechanical activity of muscle can influence NO production by the muscle in the short term, by regulating NO activity and in the long term by regulating NO expression. It was concluded from this study that NO plays a significant role in increasing glucose transport and contributing to vasodilation of vessels that supply the muscle.

Several nutrients have a positive influence on NO production. Those that are described here are relevant to the invented composition and include ascorbic acid, L-arginine, ornithine, glutamine, and folic acid.

Ascorbic acid, otherwise known as vitamin C, is a water-soluble vitamin that is an essential nutrient. It plays a role in the detoxification of potentially damaging free radicals and may be the most important antioxidant in the watery extracellular environment of the body (Kanter, et. al., 1995). Increases in oxygen consumption, body temperature, and catecholamine levels along with exercise and the acute-phase inflammatory response can lead to the promotion of free radicals. Vitamin C is able to alleviate this oxidative stress by its ability to quench singlet oxygen and the superoxide anion as well as to stabilize the hydroxyl radical.

Due to its effect as an antioxidant vitamin, C may inhibit atherogenesis and improve vascular function by two mechanisms: 1) inhibition of LDL oxidation through an LDL-specific antioxidant action, and 2) antioxidants present in cells of vascular walls decrease cellular production and release endothelial-derived nitric oxide. The most likely mechanism of ascorbic acid is either its enhancement of the availability of tetrahydrobiopterin (a co-factor for nitric oxide synthase reactions) or its increased affinity of tetrahydrobiopterin for endothelial-derived nitric oxide synthase.

Ascorbic acid has been shown to enhance impaired endothelial-derived vasodilation in patients with atherosclerosis. Nitric oxide has several vasoprotective activities, such as smooth muscle relaxation, inhibition of platelet activity, and regulation of endothelial cell permeability and adhesivity. A lack of nitric oxide may actually promote the development of atherosclerosis. The saturation of tissue with ascorbic acid provides the optimal conditions for adequate nitric oxide synthesis in endothelial cells. Decreases in cellular ascorbic acid may lead to or exacerbate the development of endothelial dysfunction. A clinical trial showed that dietary supplements of ascorbic acid prevented the development of nitrate tolerance, thus maintaining the ability of the endothelium to vasodilate (Watanabe et al 1998).

Plasma ascorbic acid levels are thought to be inversely related to the mortality from coronary artery disease. The acute application of ascorbic acid enhanced endothelial dependent vasodilation in patients with diabetes coronary artery disease, hypertension hypercholesterolemia, hyperhomocysteinemia, or chronic heat failure, and in smokers (Frei, 1999; Heller 1999).

While the Recommended Daily Allowance (RDA) for vitamin C is just 60 mg per day many of the above studies have shown that significantly higher daily doses of vitamin C can be beneficial. The current evidence suggests that heart patients would benefit from 500 to 1000 mg per day.

L-arginine (arginine) is a complex amino acid often found at the active (or catalytic) site in proteins and enzymes due to its amine-containing side chain. It is incorporated in proteins at about 4.7% on a per-mole basis when compared to the other amino acids. It is a non-essential amino acid in adults, but essential in children. Natural sources of arginine include brown rice, nuts, popcorn, raisins, and whole-wheat products.

As a precursor of nitric oxide production arginine is important for many critical physiological processes including endothelial vasodilation. In a clinical trial 5.6 to 12.6 g/day of supplemental arginine had benefits for patients with heart failure including increased blood flow, increased distances in a 6-minute walk test, and improved arterial compliance (Rector et al 1996). Others have used arginine as a treatment for high vascular resistance disorders such as hypertension, angina, cerebral ischemia and asthma (U.S. Pat. No. 5,217,997). For example, one study found that treatment with oral arginine, 6 g/day for 3 days, improved exercise capacity in patients with angina (Ceremuzynski et al 1997).

Glutamine can be a precursor to arginine and thus enhance arginine effects. In addition glutamine acts to enhance immune system after exercise and in clinical settings, while taurine has also been shown to have a benefit.

L-carnitine has been shown to increase exercise capacity in both athletes and patients with angina, presumably by increasing the availability of fatty acids for oxidative metabolism. Pyruvate and creatine are also commonly used supplements for athletic enhancement.

Folic acid (or folate) is vital for cell division and homeostasis due to the essential role of folate coenzymes in nucleic acid synthesis, methionine regeneration (from the remethylation of homocysteine), and in the shuttling, oxidation, and reduction of one-carbon units required for normal metabolism and regulation. Folate deficiency is thought to be one of the most common avitaminoses. Decreased levels of plasma folate have been linked to increased levels of plasma homocysteine, which has been known to be a causative factor in vascular disease. Brouwer et al. (1999) found significantly decreased levels of plasma homocysteine and significantly increased levels of plasma and red blood cell folate by supplementing the diet with either 500 pg/d or 250 pg/d. Plasma homocysteine levels were reduced by 22% with the 500 pg/d dose and by 11% with the 250 pg/d dose. Supplementation with folic acid in combination with vitamins B6 and B12 has been shown to be more effective at lowering homocysteine levels than supplementing with folic acid alone (Mansoor et al 1999). Mansoor showed that supplementation of 300 pg/d in healthy individuals over 5 weeks reduced plasma homocysteine levels 20% while 300 pg/d plus 120 mg/day of vitamin B6 reduced plasma homocysteine by 32%. Vitamin B12 has likewise been shown to increase the folate effect.

Normally, a wholesome diet is considered to provide sufficient amounts of these nutritive elements. Supplementation with off-the-shelf multivitamins is common. However, patients requiring improvement in cardiovascular function or peripheral vascular function often are not able or willing to prepare or choose a diet that will meet their enhanced requirements for these nutritive elements, nor do the usual vitamin supplementations provide sufficient levels for this group of patients. Therefore, it is of increased benefit to add at least these vitamins to the compositions of this invention.

The following examples are provided for illustrative purposes only and do not limit the scope of the appended claims.

EXAMPLE 1

Pliml (1992) has previously reported that 60 grams of D-Ribose daily in four 15 gram doses taken for three days benefited patients with cardiovascular disease. This dosage of ribose may bring on hypoglycemia with concomitant dizziness, nausea and sweating. Subjects frequently experience abdominal distress and diarrhea similar to that in individuals with lactose intolerance who ingest milk. Because of these unpleasant side effects, patients will be reluctant to continue ribose on a maintenance basis. Therefore, a study was done to select a lower and safer dose of ribose that is effective in increasing cardiovascular and peripheral vascular function and can be taken long-term for maintenance and cardioprotection.

A. Patient Selection and Protocol

A double-blinded, randomized, crossover clinical study was initiated to determine whether patients with cardiovascular disease could find a ribose benefit at lower, safer doses. Patients with known chronic coronary artery disease with stable angina pectoris and chronic heart failure, class II and III (New York Classification, NYHA) were selected for the study. All patients had a history and ongoing occurrences of angina pectoris. All but two patients had a previous history of myocardial infarction, with one-third having two or more previous infarcts. Thirty-one percent of the patients had a previous history of surgical intervention, either coronary artery bypass graft (CABG) or angioplasty. All patients were being treated with nitrates, molsidim and beta blockers. Three patients were also on diltiazem and an additional three on trapidil. Medications were not altered during the study. Exclusion criteria included patients <18 years of age, those with severe concurrent disease (renal failure, diabetes mellitus, neoplasia), evidence of hyperthyroidism and inability to follow the protocol.

The study consisted of two treatment periods, three weeks in duration. Initially, either ribose or placebo (dextrose) was administered three times a day with meals. Five grams of either ribose of placebo was dissolved in approximately eight ounces of fluid shortly before administration. Following the initial treatment period, the patients were given no ribose or placebo treatment for one week as a washout period. The patients were then given the alternate treatment for three weeks for the crossover phase of the study.

Measured objectives parameters of systolic and diastolic function were assessed with transthoracic echocardiography. Subjectively, quality of life using the SF36 form, and physical function (exercise tolerance) were assessed. All of the above parameters were assessed at pre- and post-treatment in both arms of the study.

B. Echocardiographic Studies

Each echocardiographic assessment was performed by the same clinical individual and accumulated data were analyzed by two cardiologists in a blinded manner, with a consensus establishing a final result. All studies were conducted with commercially available equipment (System V, GE, Norway). To allow off-line quantitative analysis of the echocardiographic data, studies were recorded on videotape with selected cine-loops and velocity spectra digitally transferred to a Macintosh G4 computer (Apple Computers, CA) for subsequent analysis. Software provided by the manufacturer (Echopac®, GE, Norway) was used for data evaluation.

Each echocardiographic assessment was performed transthoracically and a 1.7/3.4 MHZ harmonic transducer was used with the patient examined in the left lateral decubitus position. A one-lead electrocardiogram was recorded continuously during echocardiographic assessment. The M-Mode left atrial dimension was measured at end-systole in the parasternal long-axis view and left ventricular ejection fraction was determined according to the recommendations of the North American Society of Echocardiography. In addition, left atrial volume was determined using the Simpson's rule in the 4 chamber view. Transmitral Doppler inflow velocities were recorded from the apical four-chamber view with the sample volume positioned between the tips of the mitral leaflets during quiet respiration.

The parameters derived from the transmitral velocity spectra were: peak velocity of the early (E) and atrial filling (A) waves, the corresponding velocity time integrals ($VTI_E$ and $VTI_A$) and the percentage of atrial contribution to total left ventricular filling. The deceleration slope of the E wave was also measured. The percentage of atrial contribution to total left ventricular filling was determined by dividing the $VTI_A$ by the total diastolic velocity time integral. The results of five consecutive heart cycles were averaged in each patient to obtain a justified value.

C. Quality of Life and Physical Function Performance

Quality of life was assessed in each patient using the SF 36 form. These assessments were performed at baselines and at the completion of supplement administration in each arm of the study.

Semi-upright bicycle exercise tests were performed using an Ergometer device (Blitz, Germany) in a standard manner on a with incremental increase in the work load (25 watts every two minutes). All tests involved symptom limited peak exercise performance with at least an exercise induced 80-85% of age related maximal heart rate, even though most patients are on b-blocker medication. Upper extremity blood pressures were obtained by at every 2 minutes and also at peak exercise. Rate pressure product (RPP) was calculated using systolic blood pressure times heart rate and expressed in RPP units.

D. Statistical Analysis

Analysis of variance for repeated measures (ANOVA) was used for the analysis of serial changes of continuous parameters within and between the randomized, assigned treatment arms, i.e. ribose vs placebo. Further comparison were subject to Bonferroni correction. In all cases, a p value $\leq 0.05$ was considered statistically significant.

E. Conclusions

Twelve adult CHF patients underwent subjective and objective assessment, which included quality of life, physical functioning, deceleration rate of the E wave, peak velocity of the E and A waves, velocity time integral of both E and A, percentage of atrial contribution to total left ventricular filling, left atrial volume, (Table 1), left ventricular ejection fraction, left ventricular volumes, and stroke volume. All patients were compliant throughout the study and all completed both arms of the study. Patients tolerated both supplements without any adverse effects, including systemic and pulmonary-cardiovascular events.

TABLE I

| THERAPY | Edc* | SVI* | EF | Ac# | LVVs* |
|---|---|---|---|---|---|
| Ribose | 193.5 ± 45.9 | 2.63 ± .57 | 51.0 ± 7.3 | 45.3 ± 9.2 | 64.4 ± 24.8 |
| Dextrose | 250 ± 70.2 | 1.99 ± .71 | 40.9 ± .71 | 39.2 ± 9.7 | 78.4 ± 27.0 |

*($p \leq .005$, #p < .01)

ECHO revealed a significant improvement in deceleration time of the E wave (Edc in msec), stroke volume index (SVI, ml/body mass index) ejection fraction (EF, %), atrial contribution (Ac, &), and left ventricular systolic volume (LVVs, ml) in the ribose. Analysis of parameters reflecting diastolic function revealed significant findings. Ribose demonstrated a significant shorter deceleration time of the E wave, with a significantly smaller left atria volume and a higher atrial contribution to left ventricular filling as compared to patients treated with placebo.

All patients completed exercise testing without any adverse effects. The mean maximal attained exercise level was not changed by either treatment, beginning vs at the end of the treatment period. On the other hand, a noted difference in quality of life and physical functioning was observed between modalities. Patients receiving oral ribose demonstrated a significant improvement in the overall score of the quality of life index. This increase was paralleled by a significant improvement in physical function.

Over a relatively short term, treatment with oral D-ribose significantly improved diastolic cardiac function in patients with severe coronary artery disease and congestive heart failure. Administration of ribose resulted in an enhanced quality of life. Longer term studies with ribose supplementation and studies on less severely ill patients are expected to show greater improvement in diastolic and systolic function. In the absence of adverse effects, it is recommended that patients continue on a maintenance method of at least one dose of ribose daily.

EXAMPLE 2

Compositions of Ribose with Other Components

It has been shown in other studies that the beneficial effects of ribose are augmented in subjects with poor circulation by the concomitant administration of vasodilators, which relax the blood vessels, allowing better circulation and hence better accessibility of ribose to the tissues. It can be noted in Example 1 that these severely ill patients are all taking at least one vasodilator. Nitrates, especially nitroglycerine, are most commonly used because of their rapid onset of action. Patients experiencing angina self-administer nitrates buccally, sublingually or transdermally, since nitrates administered orally are quickly cleared on passage through the liver. Even when administered in this manner, nitrates have a very short half-life in the body. Nitrates are not a pleasant therapy, often causing severe headaches. It is beneficial to administer a vasodilator with ribose in order improve circulation, thereby making ribose more available to the tissues. Ribose is most conveniently administered orally. Therefore, in order to have the maximum benefits in subjects in which the vasodilator cannot be administered orally, it is advised to ingest ribose about fifteen minutes before administration of the vasodilator. This minor inconvenience may be eliminated when the vasodilator selected may be administered orally. Therefore, the compositions below incorporate L-arginine or its equivalents as a vasodilator. Other useful orally administered vasodilators include L-arginine, nitroglycerine, nitrates, nitrites, papaverine, isoproterenol, nylidrin, isoxsuprine, nitroprusside, adenosine, xanthine, ethyl alcohol, dipyramide, hydrazaline, minoxidil, diazoxide or analogs of the foregoing.

Subjects also may have suboptimal circulation or be in a suboptimal nutritional state. Accordingly, the following compositions have been made to provide additional benefit to the cardiac patient, especially to the patient undergoing rehabilitation, and to subjects needing cardioprotection.

The following compositions are to be taken one to four times per day:

| | PREFERRED DOSE | ACCEPTABLE RANGE |
|---|---|---|
| | COMPOSITION A | |
| D-ribose | 5 g | 1-20 g |
| L-arginine | 2 g | 0*-8 g |
| | COMPOSITION B | |
| D-ribose | 5 g | 1-20 g |
| Glucose | 5 g | 0-20 g (to equal ribose amount) |
| L-arginine | 2 g | 0*-8 g |
| Glutamine | 500 mg | 40-1000 mg |
| Vitamin C | 500 mg | 100-1000 mg |
| Folic acid | 0.2 mg | 0.1-1.0 mg |
| Vitamin B12 | 0.25 mg | 0.1-1.0 mg |
| Vitamin B6 | 6 mg | 1-50 mg |

*arginine can be replaced by citrulline or ornithine or other orally administered vasodilators The ingredients are triturated as a dry powder. The powder can be conveniently dissolved in any carrier, preferably one that comprises a pleasant flavoring and color. Many patients will prefer a sweeter composition. Sweeteners such as sucrose or corn syrup or the like can easily be added to taste. It may be most convenient to prepare a concentrated liquid solution to be diluted by the patient with water or other liquid.

EXAMPLE 4

Additional Useful Ingredients

Any of the above compositions, or ribose alone, can be supplemented with one or any combination of L-carnitine, taurine, creatine, coenzyme Q10, and/or pyruvate. Supplementation with any or all of these compounds will incrementally improve cardiovascular or peripheral vascular function and provide cardioprotection against onset or recurrence of cardiovascular or peripheral vascular disease.

EXAMPLE 5

The following study was devised to check the benefits of additions to the basic ribose treatment.

Patients recovering from recent myocardial infarction will be selected according to these entrance criteria:
- Adult (male/female) $\geq$21 years of age
- Enrolled in a cardiac rehabilitation program $\geq$eight weeks or under medical supervision
- Patients with ejection fraction $\leq$30% or Class IV heart failure will be excluded
- No symptomatic chronic obstructive pulmonary disease
- No symptomatic peripheral vascular disease
- No uncontrolled high blood pressure
- No history of TIAs or CVAs
- No condition that would prohibit treadmill or bicycling exercise
- Patients must fail two (2) baseline treadmill tests
- Type II diabetic patients are eligible One hundred patients (20 patients at each of five sites) who have been enrolled in a cardiac rehabilitation program of $\geq$ eight weeks duration will be enrolled in a study. Once informed consent has been obtained, patients will undergo two baseline exercise (treadmill or cycling) assessments, as well as a baseline quality of life questionnaire. Whichever exercise assessment the patient begins, the patient must continue on this type of exercise throughout the protocol period. Blind randomizations will then occur.

After baseline assessment and randomization, as a pilot study, four patients at each site will begin oral supplementation with Composition B. Four patients at each site will be given a placebo consisting of 5 g glucose. The supplementation will be taken twice a day, around mealtime. All patients will discontinue supplementation after eight weeks. During the supplementation period, at week eight and each week for two weeks following discontinuation of exercise assessment, patients will undergo an evaluation consisting of exercise assessment and a quality of life questionnaire. In addition, any non-insulin dependent diabetics will have daily serum glucose levels drawn for the first weeks after beginning oral supplementation.

The exercise assessment will include type of exercise test (treadmill or bicycling) duration of exercise (time), grade or level of exercise (resistance), and physical restraints or symptoms while or shortly after each exercise bout. EKG tracings will be taken to monitor cardiovascular or anginal changes. The same type of exercise test will be used for each evaluation in a specific patient for comparison purposes. Additionally, as assessment will be made as to potential rate of increase in activity (exercise)/time in cardiac rehabilitation for each designated tested time point.

It is expected that the patients given the composition of this invention will be able to exercise longer, at a higher level and without restraint or cardiac symptoms than in those patients receiving placebo. It is further expected that the reported quality of life will be more favorable in the patients receiving the composition of this invention than in those receiving placebo.

EXAMPLE 6

Treatment of Hypertension

As shown in Example 1, treatment with ribose improves diastolic cardiac function. Since hypertension is accompanied by left ventricular dysfunction, it is expected that the administration of ribose to patients experiencing hypertension with result in a benefit. One subject has been tested. Her blood pressure has been tested at borderline values of 130/90. Following daily administration of ribose at 5-10 grams per day, her blood pressure was lowered to as low as 108/78. Further studies with ribose alone or with Composition A are expected to confirm the pressure-lowering effects of ribose administration.

All references cited within are hereby incorporated by reference. It will be understood by those skilled in the art that variations and substitutions may be made in the invention without departing from the spirit and scope of this invention.

We claim:

1. A method for improving the cardiovascular function of a subject having reduced cardiovascular function consisting of the administration of two to eight grams of D-ribose one to four times daily to the subject for a period of three weeks.

2. A method for improving the cardiovascular function of a subject having reduced cardiovascular function comprising the administration of two to eight grams of D-ribose plus an effective amount of a vasodilator one to four times daily to the subject for a period of three weeks.

3. The method according to claim 2 wherein the vasodilator is L-arginine, nitroglycerin, a nitrate, a nitrite, papaverine, isoproterenol, nylidrin, isoxsuprine, nitroprusside, adenosine, xanthine, ethyl alcohol, dipyramide, hydrazaline, minoxidil or diazoxide.

* * * * *